United States Patent
Kullas et al.

(10) Patent No.: US 8,221,440 B2
(45) Date of Patent: Jul. 17, 2012

(54) METHOD AND APPARATUS FOR DELIVERING A PROSTHETIC FABRIC INTO A PATIENT

(75) Inventors: Karen E. Kullas, Taunton, MA (US); Daniel E. Hass, West Greenwich, RI (US); Thomas J. Capuzziello, Milford, MA (US); Dennis J. Coffey, Foster, RI (US); David C. Calabrese, North Kingston, RI (US)

(73) Assignee: C.R. Bard, Inc., Murray Hill, NJ (US)

(*) Notice: Subject to any disclaimer, the term of this patent is extended or adjusted under 35 U.S.C. 154(b) by 0 days.

(21) Appl. No.: 12/941,686

(22) Filed: Nov. 8, 2010

(65) Prior Publication Data
US 2011/0054485 A1    Mar. 3, 2011

Related U.S. Application Data

(62) Division of application No. 10/855,803, filed on May 27, 2004, now Pat. No. 7,846,171.

(51) Int. Cl.
*A61B 17/02*    (2006.01)

(52) U.S. Cl. .................. 606/151; 606/213; 604/15

(58) Field of Classification Search .............. 606/108, 606/151–156, 213–217; 623/1.11, 1.12; 604/15–17, 57–64
See application file for complete search history.

(56) References Cited

U.S. PATENT DOCUMENTS

| | | | |
|---|---|---|---|
| 636,637 A | 11/1899 | Cooke | |
| 654,564 A | 7/1900 | Dargatz | |
| 689,256 A | 12/1901 | Walsh | |
| 700,139 A | 5/1902 | Fuller | |
| 702,997 A | 6/1902 | Pugh | |
| 1,131,349 A | 3/1915 | Ellis | |
| 1,456,828 A | 5/1923 | Pistor | |
| 1,712,084 A | 5/1929 | Irving | |
| 2,091,438 A | 8/1937 | Morley | |
| 2,235,979 A | 3/1941 | Brown | |
| 2,524,195 A | 10/1950 | Hoover | |

(Continued)

FOREIGN PATENT DOCUMENTS

CA    2098683    12/1993

(Continued)

OTHER PUBLICATIONS 510K submission, Folder K930147, Document MFRREDACT: Nov. 18, 1999, Surgical Mesh Delivery System, 165 pages.

*Primary Examiner* — Kathleen Sonnett
(74) *Attorney, Agent, or Firm* — Wolf, Greenfield & Sacks, P.C.

(57) ABSTRACT

An introducer and method for delivering a prosthetic fabric into a patient. The introducer includes a delivery tube having a distal end adapted to be inserted into the patient and a lumen that receives the prosthetic fabric. A loader may be provided to reconfigure the prosthetic fabric from a first configuration to a collapsed configuration and/or to insert the collapsed fabric into the lumen of the delivery tube. A plunger may be provided to push the prosthetic fabric through the delivery tube and into the patient. The loader and plunger may be combined in a dual-purpose component that is reversible to either load the fabric into the delivery tube or push the fabric through the delivery tube.

7 Claims, 10 Drawing Sheets

U.S. PATENT DOCUMENTS

| | | |
|---|---|---|
| 2,829,649 A | 4/1958 | Glenner |
| 2,886,004 A | 5/1959 | Morrison |
| 3,015,332 A | 1/1962 | Brecht |
| 3,086,527 A | 4/1963 | Forrest |
| 3,108,594 A | 10/1963 | Glassman |
| 3,138,159 A | 6/1964 | Schmidt |
| 3,508,554 A | 4/1970 | Sheridan |
| 3,699,962 A | 10/1972 | Hanke |
| 3,731,671 A | 5/1973 | Mageoh |
| 3,918,452 A | 11/1975 | Cornfeld |
| 3,927,672 A | 12/1975 | Garcia |
| 3,944,641 A | 3/1976 | Lemelson |
| 3,948,273 A | 4/1976 | Sanders |
| 4,177,814 A | 12/1979 | Knepshield et al. |
| 4,232,660 A | 11/1980 | Coles |
| 4,291,696 A | 9/1981 | Ring |
| 4,301,806 A | 11/1981 | Helfer |
| 4,330,497 A | 5/1982 | Agdanowski |
| 4,410,476 A | 10/1983 | Redding et al. |
| 4,461,281 A | 7/1984 | Carson |
| 4,479,791 A | 10/1984 | Sprague |
| 4,509,516 A | 4/1985 | Richmond |
| 4,539,976 A | 9/1985 | Sharpe |
| 4,573,448 A | 3/1986 | Kambin |
| 4,573,964 A | 3/1986 | Huffman |
| 4,586,491 A | 5/1986 | Carpenter |
| 4,670,618 A | 6/1987 | Bellinger |
| 4,723,547 A | 2/1988 | Kullas et al. |
| 4,738,248 A | 4/1988 | Ray |
| 4,768,507 A * | 9/1988 | Fischell et al. ............... 623/1.11 |
| 4,790,819 A * | 12/1988 | Li et al. ............................ 604/59 |
| 4,817,598 A | 4/1989 | LaBombard |
| 4,840,623 A | 6/1989 | Quackenbush |
| 4,895,559 A | 1/1990 | Shippert |
| 4,931,039 A | 6/1990 | Coe et al. |
| 4,943,282 A | 7/1990 | Page et al. |
| 4,946,444 A | 8/1990 | Heimke et al. |
| 4,959,067 A | 9/1990 | Muller |
| 4,972,827 A | 11/1990 | Kishi et al. |
| 4,994,027 A | 2/1991 | Farrell |
| 5,007,895 A | 4/1991 | Burnett |
| 5,021,059 A | 6/1991 | Kensey et al. |
| 5,036,854 A | 8/1991 | Schollmeyer et al. |
| 5,053,016 A | 10/1991 | Lander |
| 5,066,288 A | 11/1991 | Deniega et al. |
| 5,071,410 A | 12/1991 | Pazell |
| 5,074,840 A | 12/1991 | Yoon |
| 5,074,867 A | 12/1991 | Wilk |
| 5,116,357 A | 5/1992 | Eberbach |
| 5,122,155 A | 6/1992 | Eberbach |
| 5,135,510 A | 8/1992 | Maszkiewicz et al. |
| 5,141,515 A | 8/1992 | Eberbach |
| 5,147,374 A | 9/1992 | Fernandez |
| 5,147,387 A | 9/1992 | Jansen et al. |
| 5,158,543 A | 10/1992 | Lazarus |
| 5,176,692 A | 1/1993 | Wilk et al. |
| 5,178,623 A | 1/1993 | Cinberg et al. |
| 5,180,373 A | 1/1993 | Green et al. |
| 5,192,302 A | 3/1993 | Kensey et al. |
| 5,209,736 A | 5/1993 | Stephens et al. |
| 5,244,619 A | 9/1993 | Burnham |
| 5,258,000 A | 11/1993 | Gianturco |
| 5,263,969 A | 11/1993 | Phillips |
| 5,275,611 A | 1/1994 | Behl |
| 5,292,332 A | 3/1994 | Lee |
| 5,304,187 A | 4/1994 | Green et al. |
| 5,310,407 A | 5/1994 | Casale |
| 5,316,543 A | 5/1994 | Eberbach |
| 5,320,639 A | 6/1994 | Rudnick |
| 5,333,624 A | 8/1994 | Tovey |
| 5,334,169 A | 8/1994 | Brown et al. |
| 5,350,387 A | 9/1994 | Semm |
| 5,354,302 A | 10/1994 | Ko |
| 5,366,460 A | 11/1994 | Eberbach |
| 5,370,646 A | 12/1994 | Reese et al. |
| 5,370,650 A | 12/1994 | Tovey et al. |
| 5,383,477 A | 1/1995 | DeMatteis |
| 5,387,224 A | 2/1995 | Semm |
| 5,395,317 A | 3/1995 | Kambin |
| 5,395,383 A | 3/1995 | Adams et al. |
| 5,397,331 A | 3/1995 | Himpens et al. |
| 5,397,332 A | 3/1995 | Kammerer et al. |
| 5,403,264 A | 4/1995 | Wohlers et al. |
| 5,404,887 A | 4/1995 | Prather |
| 5,405,360 A | 4/1995 | Tovey |
| 5,405,379 A * | 4/1995 | Lane ............................ 623/1.2 |
| 5,431,676 A | 7/1995 | Dubrul et al. |
| 5,437,644 A | 8/1995 | Nobles |
| 5,453,090 A * | 9/1995 | Martinez et al. .............. 606/108 |
| 5,456,714 A | 10/1995 | Owen |
| 5,464,403 A | 11/1995 | Kieturakis et al. |
| 5,466,239 A | 11/1995 | Cinberg et al. |
| 5,484,444 A | 1/1996 | Braunschweiler et al. |
| 5,490,843 A | 2/1996 | Hildwein et al. |
| 5,496,292 A | 3/1996 | Burnham |
| 5,503,623 A | 4/1996 | Tilton, Jr. |
| 5,514,158 A | 5/1996 | Kanesaka |
| 5,540,711 A | 7/1996 | Kieturakis et al. |
| 5,554,133 A | 9/1996 | Haffner et al. |
| 5,607,443 A | 3/1997 | Kieturakis et al. |
| 5,630,801 A * | 5/1997 | Roussigne et al. ........... 623/1.11 |
| 5,630,830 A | 5/1997 | Verbeek |
| 5,647,846 A | 7/1997 | Berg et al. |
| 5,681,296 A | 10/1997 | Ishida |
| 5,693,089 A * | 12/1997 | Inoue ........................... 128/898 |
| 5,695,525 A | 12/1997 | Mulhauser et al. |
| 5,702,416 A | 12/1997 | Kieturakis et al. |
| 5,716,369 A | 2/1998 | Riza |
| 5,718,675 A | 2/1998 | Leijd |
| 5,730,756 A | 3/1998 | Kieturakis et al. |
| 5,759,186 A | 6/1998 | Bachmann et al. |
| 5,762,629 A | 6/1998 | Kambin |
| 5,762,631 A | 6/1998 | Klein |
| 5,766,157 A | 6/1998 | Tilton, Jr. |
| 5,766,246 A | 6/1998 | Mulhauser et al. |
| 5,776,115 A | 7/1998 | Antoshkiw et al. |
| 5,782,860 A | 7/1998 | Epstein et al. |
| 5,792,116 A | 8/1998 | Berg et al. |
| 5,797,882 A | 8/1998 | Purdy et al. |
| 5,797,899 A | 8/1998 | Tilton, Jr. |
| 5,800,362 A | 9/1998 | Kobren et al. |
| 5,800,398 A | 9/1998 | Hähnle et al. |
| 5,810,711 A | 9/1998 | Scheyer |
| 5,814,058 A | 9/1998 | Carlson et al. |
| 5,817,102 A | 10/1998 | Johnson et al. |
| 5,817,123 A | 10/1998 | Kieturakis et al. |
| 5,824,027 A | 10/1998 | Hoffer et al. |
| 5,833,707 A * | 11/1998 | McIntyre et al. .............. 606/198 |
| 5,836,961 A | 11/1998 | Kieturakis et al. |
| 5,871,498 A | 2/1999 | Jervis et al. |
| 5,885,508 A | 3/1999 | Ishida |
| 5,911,712 A | 6/1999 | Leutwyler et al. |
| 5,911,714 A | 6/1999 | Wenstrom, Jr. |
| 5,913,818 A | 6/1999 | Co et al. |
| 5,919,184 A | 7/1999 | Tilton, Jr. |
| 5,941,910 A | 8/1999 | Schindler et al. |
| 5,954,729 A | 9/1999 | Bachmann et al. |
| 5,957,836 A | 9/1999 | Johnson |
| 5,957,939 A * | 9/1999 | Heaven et al. ................. 606/151 |
| 5,971,920 A | 10/1999 | Nagel |
| 5,984,904 A | 11/1999 | Steen et al. |
| 5,993,473 A | 11/1999 | Chan et al. |
| 6,004,337 A | 12/1999 | Kieturakis et al. |
| 6,007,487 A | 12/1999 | Foley et al. |
| 6,033,361 A | 3/2000 | Co et al. |
| 6,080,168 A | 6/2000 | Levin et al. |
| 6,156,045 A | 12/2000 | Ulbrich et al. |
| 6,171,282 B1 | 1/2001 | Ragsdale |
| 6,179,826 B1 | 1/2001 | Aebischer et al. |
| 6,193,731 B1 | 2/2001 | Oppelt et al. |
| 6,196,968 B1 | 3/2001 | Rydin et al. |
| 6,214,020 B1 | 4/2001 | Mulhauser et al. |
| 6,228,024 B1 | 5/2001 | Co et al. |
| 6,258,113 B1 | 7/2001 | Adams et al. |
| 6,264,604 B1 | 7/2001 | Kieturakis et al. |
| 6,267,772 B1 | 7/2001 | Mulhauser et al. |
| 6,312,442 B1 | 11/2001 | Kieturakis et al. |

| | | |
|---|---|---|
| 6,352,561 B1 | 3/2002 | Leopold et al. |
| 6,368,337 B1 | 4/2002 | Kieturakis et al. |
| 6,375,774 B1 | 4/2002 | Lunn et al. |
| 6,416,465 B2 | 7/2002 | Brau |
| 6,416,506 B1 | 7/2002 | Tilton, Jr. et al. |
| 6,425,859 B1 | 7/2002 | Foley et al. |
| 6,425,915 B1 | 7/2002 | Khosravi et al. |
| 6,428,546 B1 | 8/2002 | Cancel et al. |
| 6,440,120 B1 | 8/2002 | Maahs |
| 6,447,533 B1 | 9/2002 | Adams |
| 6,478,803 B1 | 11/2002 | Kapec et al. |
| 6,514,272 B1 | 2/2003 | Kieturakis et al. |
| 6,575,988 B2 | 6/2003 | Rousseau |
| 7,137,993 B2 * | 11/2006 | Acosta et al. ............... 623/1.11 |
| 7,279,177 B2 * | 10/2007 | Looney et al. ............... 424/443 |
| 2001/0031972 A1 | 10/2001 | Robertson et al. |
| 2001/0034535 A1 | 10/2001 | Schultz |
| 2002/0013514 A1 | 1/2002 | Brau |
| 2002/0029077 A1 | 3/2002 | Leopold et al. |
| 2002/0055747 A1 | 5/2002 | Cano et al. |
| 2002/0062129 A1 | 5/2002 | Mikus et al. |
| 2002/0082622 A1 | 6/2002 | Kane |
| 2002/0151859 A1 | 10/2002 | Schoelling |
| 2003/0045789 A1 | 3/2003 | Thompson et al. |
| 2003/0050644 A1 | 3/2003 | Boucher et al. |
| 2003/0120223 A1 | 6/2003 | Von Segesser |
| 2003/0236485 A1 | 12/2003 | Fedyk et al. |
| 2004/0010263 A1 | 1/2004 | Boucher et al. |
| 2004/0073193 A1 | 4/2004 | Houser et al. |
| 2004/0082969 A1 | 4/2004 | Kerr |
| 2004/0092970 A1 | 5/2004 | Xavier |
| 2004/0093061 A1 * | 5/2004 | Acosta et al. ............... 623/1.11 |
| 2004/0097877 A1 | 5/2004 | Stecker |
| 2004/0097958 A1 | 5/2004 | Whitman et al. |

FOREIGN PATENT DOCUMENTS

| | | |
|---|---|---|
| EP | 0 349 222 | 1/1990 |
| EP | 0 392 281 | 10/1990 |
| EP | 0 535 506 | 9/1992 |
| EP | 0 517 608 | 12/1992 |
| EP | 0 519 022 | 12/1992 |
| EP | 0 544 485 | 6/1993 |
| EP | 0 581 036 | 2/1994 |
| EP | 0 614 650 | 9/1994 |
| EP | 0 625 334 | 11/1994 |
| EP | 1 101 454 | 5/2001 |
| EP | 0 956 060 | 6/2004 |
| FR | 2 705 225 | 11/1994 |
| FR | 2 710 518 | 4/1995 |
| GB | 2 097 259 | 11/1982 |
| GB | 2 254 788 | 10/1992 |
| WO | WO 92/05828 | 4/1992 |
| WO | WO 92/06638 | 4/1992 |
| WO | WO 92/06639 | 4/1992 |
| WO | WO 92/13500 | 8/1992 |
| WO | WO 94/27535 | 12/1994 |
| WO | WO 95/30374 | 11/1995 |
| WO | WO 96/21487 | 7/1996 |
| WO | WO 96/41588 | 12/1996 |
| WO | WO 03/045467 | 6/2003 |

* cited by examiner

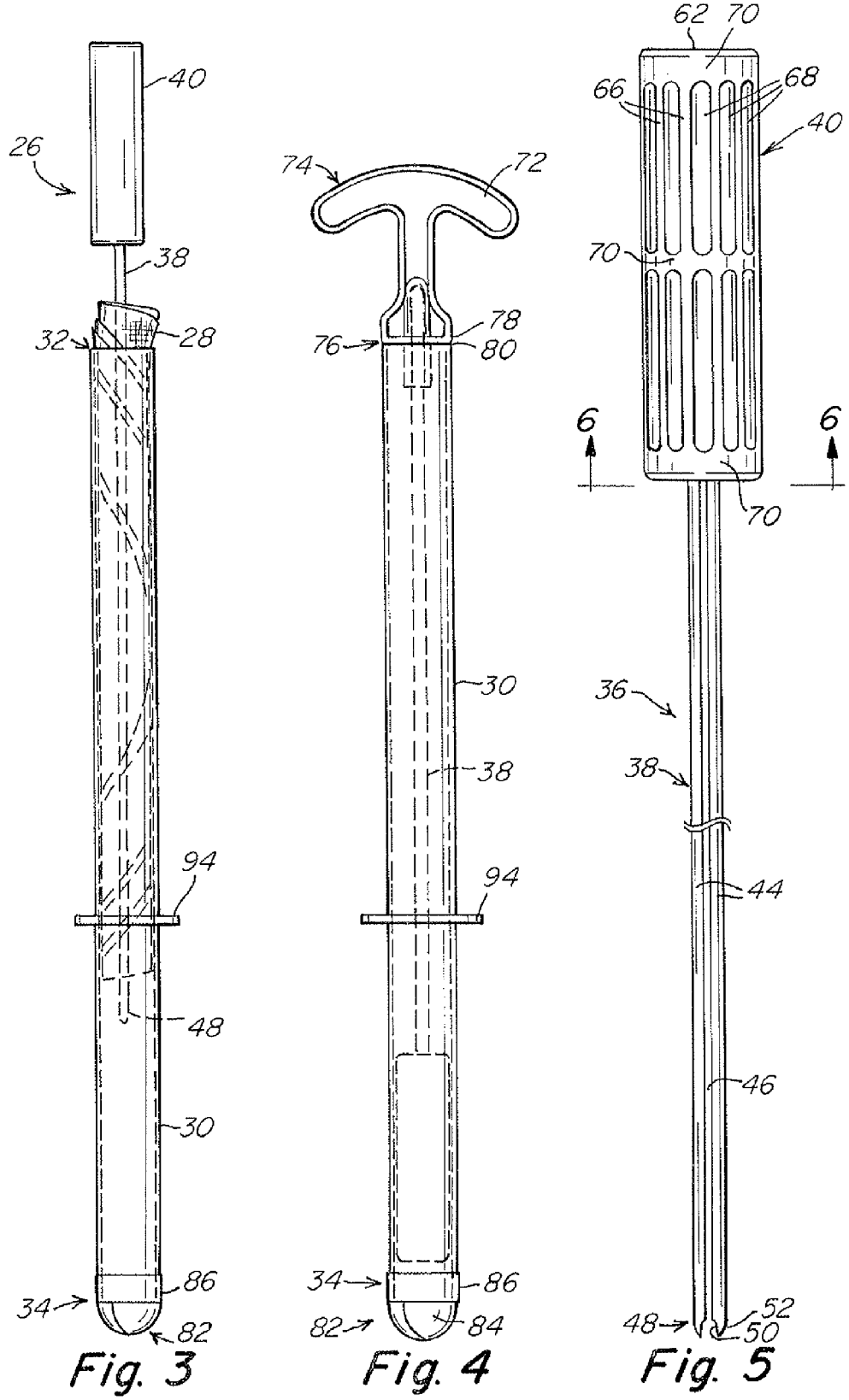

METHOD AND APPARATUS FOR DELIVERING A PROSTHETIC FABRIC INTO A PATIENT

RELATED APPLICATION(S)

This application is a divisional of U.S. application Ser. No. 10/855,803, filed May 27, 2004, now U.S. Pat. No. 7,846,171.

FIELD OF THE INVENTION

The present invention relates to a device and a method for delivering a prosthetic fabric into a patient.

DISCUSSION OF RELATED ART

Various prosthetic repair fabrics are employed by surgeons for soft tissue repair and reconstruction, including the repair of anatomical defects such as tissue and muscle hernias. For example, a ventral hernia in the abdominal wall is commonly repaired using a sheet of biocompatible fabric, such as a knitted polypropylene mesh (BARD MESH) or a composite fabric that includes a mesh and an adhesion resistant barrier (COMPOSIX E/X MESH). The fabric is typically sutured, stapled or otherwise provisionally anchored in place over, under or within the defect. Tissue integration with the fabric, such as tissue ingrowth into and/or along the mesh fabric, eventually completes the repair. An adhesion resistant barrier, if provided, prevents tissue ingrowth to one or more selected portions of the mesh fabric.

Various surgical techniques may be employed for soft tissue repair, including open, laparoscopic and hybrid (e.g., Kugel procedure). During a laparoscopic procedure, the prosthetic fabric may be routed to the surgical site through a slender laparoscopic cannula. The fabric is typically collapsed, such as by rolling or folding, into a reduced configuration to facilitate its passage through the narrow cannula. Certain repairs, such as laparoscopic repair of ventral hernias, may require large sheets of prosthetic fabric that may be difficult to deliver laparoscopically or through a laparoscopic-like "hybrid" procedure. Devices have been proposed to facilitate delivery of repair fabric into a patient. Examples of such devices are disclosed in U.S. Pat. Nos. 5,147,374; 5,304,187; 5,350,387; and 5,695,525.

It is an object of the present invention to provide a method and apparatus for delivering a prosthetic fabric into a patient.

SUMMARY OF THE INVENTION

In one illustrative embodiment of the invention, a method is provided for delivering a prosthetic fabric into a patient. The method comprises acts of collapsing the prosthetic fabric from a first configuration to a collapsed configuration; loading the prosthetic fabric in the collapsed configuration into a delivery tube using a dual-purpose component in the first orientation; reversing the dual-purpose component from the first orientation to a second orientation; and expelling the prosthetic fabric in the collapsed configuration from a distal end of the delivery tube using the dual-purpose component in the second orientation.

In another illustrative embodiment of the invention, an introducer is provided for delivering a prosthetic fabric into a patient. The introducer comprises a delivery tube having a distal end adapted to be inserted into the patient and a lumen extending therethrough that is adapted to receive the prosthetic fabric. The introducer also comprises a dual-purpose component including a first portion to load the prosthetic fabric into the delivery tube and a second portion to push the prosthetic fabric through the lumen. The first portion and the second portion have different configurations. The dual-purpose component is reversibly insertable into the lumen in one of a first orientation to load the prosthetic fabric into the delivery tube with the first portion and a second orientation to push the prosthetic fabric through the delivery tube with the second portion.

In a further illustrative embodiment of the invention, an introducer is provided for delivering a prosthetic fabric into a patient. The introducer comprises a delivery tube having a distal end adapted to be inserted into the patient and a lumen extending therethrough that is adapted to receive the prosthetic fabric therein. The introducer also comprises a closure that is disposed on the delivery tube. The closure is operable between a closed position to at least partially obstruct the lumen and an open position to allow passage of the prosthetic fabric from the delivery tube through the lumen. The introducer further comprises a loader to reconfigure the prosthetic fabric to a collapsed configuration that is moveable along the lumen.

In another illustrative embodiment of the invention, an introducer is provided for delivering a prosthetic fabric into a patient. The introducer comprises a delivery tube having a distal end adapted to be inserted into the patient and a textured internal surface adapted to contact the prosthetic fabric as the prosthetic fabric is advanced through the delivery tube. The textured internal surface is constructed and arranged to present a contact area between the prosthetic fabric and the delivery tube that is less than a contact area between the prosthetic fabric and a smooth internal surface. The introducer also comprises a plunger to push the prosthetic fabric through the lumen of the delivery tube.

In a further illustrative embodiment of the invention, an introducer is provided for delivering a prosthetic fabric into a patient. The introducer comprises a delivery tube having a distal end adapted to be inserted into the patient and a lumen extending therethrough that is adapted to receive the prosthetic fabric. The introducer also comprises a dual-purpose component including a pair of opposed tines to load the prosthetic fabric into the delivery tube and a body portion to push the prosthetic fabric through the lumen. The body portion has an outer periphery constructed and arranged to conform to an inner wall of the delivery tube and the pair of opposed tines extends from an end of the body portion in a longitudinal direction. The dual-purpose component is reversibly insertable into the lumen in one of a first orientation to load the prosthetic fabric into the delivery tube with the pair of opposed tines and a second orientation to push the prosthetic fabric through the delivery tube with the body portion. The introducer further comprises a closure that is disposed at the distal end of the delivery tube. The closure is operable between a closed position to at least partially obstruct the lumen and an open position to allow passage of the prosthetic fabric from the delivery tube through the lumen.

In yet another illustrative embodiment of the invention, a method is provided for delivering a prosthetic fabric into a patient. The method comprises acts of collapsing the prosthetic fabric external to a delivery tube using a loader to form a collapsed prosthetic fabric; placing the collapsed prosthetic fabric into the delivery tube with the loader; and removing the loader from the delivery tube while maintaining the collapsed prosthetic fabric in the delivery tube.

In yet a further illustrative embodiment of the invention, a method is provided for replacing a first laparoscopic instrument in an incision with a second laparoscopic instrument.

The method comprises acts of inserting a switching stick into the incision through a lumen of the first laparoscopic instrument; removing the first instrument from the incision while maintaining the switching stick in the incision; and guiding an external surface of the second laparoscopic instrument along the switching stick and into the incision.

BRIEF DESCRIPTION OF THE DRAWINGS

Various embodiments of the invention will now be described, by way of example, with reference to the accompanying drawings, in which:

FIG. 3 is a side view of an introducer of FIG. 1 in the first configuration with a prosthetic fabric loaded in the delivery tube;

FIG. 4 is a side view of the introducer of FIG. 2 in the second configuration;

FIG. 5 is a side view of a dual-purpose component that may be employed as a loader and/or a plunger according to one illustrative embodiment of the invention;

DETAILED DESCRIPTION

Figure 1:
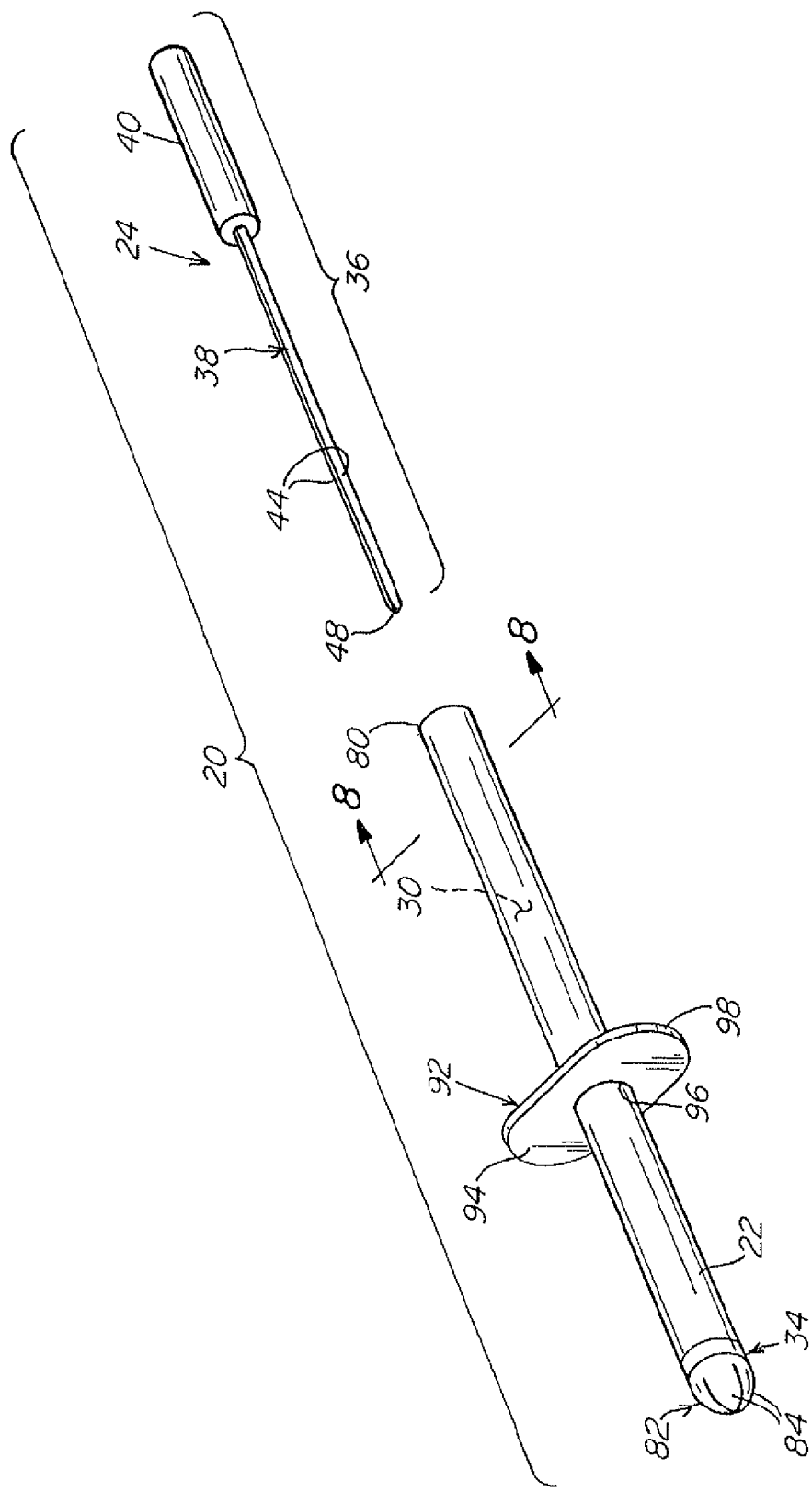
FIG. 1 is an exploded perspective view of an introducer in a first configuration according to one illustrative embodiment of the invention.

Embodiments of the present invention include an introducer and method for delivering a prosthetic fabric into a patient. The introducer may include a delivery tube that is insertable into the patient and is adapted to receive and pass the fabric therethrough into the patient. A loader may be provided to reconfigure and/or insert the prosthetic fabric into the delivery tube. A plunger may be provided to expel the fabric from the delivery tube and into the patient.

In one embodiment, the loader may include an elongated rod with a pair of opposed tines to receive a portion of the fabric therebetween. The tines may extend from an end of a handle that is configured to be manipulated by a user to collapse the fabric about the tines. In this regard, the loader may be configured to roll the fabric about the tines by rotating the handle. The collapsed fabric may then be loaded into a lumen of the delivery tube using the loader.

In one embodiment, the plunger may include a plunger head that is configured to be pushed through the lumen of the tube to expel the loaded fabric from the delivery tube. The plunger head may be configured to closely conform to the lumen.

Rather than separate devices for the loader and the plunger, a dual-purpose component that acts as both a loader and a plunger may be employed in one embodiment of the introducer. The dual-purpose component may be used in a first orientation to load the fabric into the delivery tube, and then reversed to a second orientation and reinserted into the delivery tube to expel the fabric. The dual-purpose component may include a body portion that can be used as the loader handle when employed as a loader or the plunger head when employed as a plunger. A rod may extend from an end of the body portion to be used to reconfigure the fabric and insert the collapsed fabric into the tube when employed as the loader. The rod may also be used to exert force against the plunger head when the dual-purpose component is employed as a plunger.

A closure, which is operable between a closed position to at least partially obstruct the lumen and an open position to allow passage of the prosthetic fabric into the patient, may be provided in one embodiment of the tube. The closure may be located at the distal end of the delivery tube to prevent debris, such as from coring of tissue, from entering the lumen. The closure may also reduce potential leakage of pressure from the internal cavity of the patient when the introducer is inserted through the incision during a laparoscopic procedure. The closure may be configured, such as with a hemispherical shape, to facilitate insertion of the delivery tube through an incision in the patient.

The delivery tube may be configured to reduce the amount of surface adhesion between the tube and the loaded fabric so that the fabric may be easily expelled from the tube. In one embodiment, the tube may be provided with a textured, internal surface that reduces the contact area between the tube and the prosthetic fabric to reduce the amount of surface adhesion or tension that would otherwise occur if the tube employed a smooth internal surface.

The introducer may be employed to deliver a sheet of prosthetic repair fabric, such as a generally flat prosthetic fabric or a more complex, three-dimensional prosthetic fabric. The introducer may be used to deliver repair fabrics having various characteristics. For example, the repair fabric may promote tissue ingrowth therein, such as a knitted mesh fabric, inhibit tissue ingrowth therein, or provide both tissue ingrowth and adhesion resistant characteristics.

In one illustrative embodiment as shown in FIGS. 1-4, the introducer 20 includes a delivery tube 22, a loader 24 and a plunger 26. The delivery tube is configured to be inserted into a patient for delivery of a prosthetic fabric 28 that is loaded in the tube 22. The loader 24 is used to load the prosthetic fabric into the tube. In some embodiments, the loader may also be employed to collapse the prosthetic fabric 28 into a configuration suitable for loading into the delivery tube 22. The plunger 26 is used to push the fabric 28 through the delivery tube 22. It is to be appreciated that the introducer does not require both the loader and the plunger in all embodiments of the invention and that other embodiments of the introducer may be provided with either a loader or a plunger.

The delivery tube 22 is configured to receive and house the prosthetic fabric 28 pending delivery into a patient. In one illustrative embodiment, the delivery tube 22 has an elongated tubular configuration with a lumen 30 that extends from a proximal end 32 to a distal end 34. The lumen 30 is adapted to receive a collapsed prosthetic fabric 28 through the proximal end of the tube using the loader 24. Once inserted into a patient, such as through a surgical incision 100, a naturally occurring orifice or another surgical instrument, the collapsed fabric may be pushed through the lumen 30 using the plunger 26 so that it is expelled from the distal end 34 of the tube 22 and into the patient.

Figure 2:
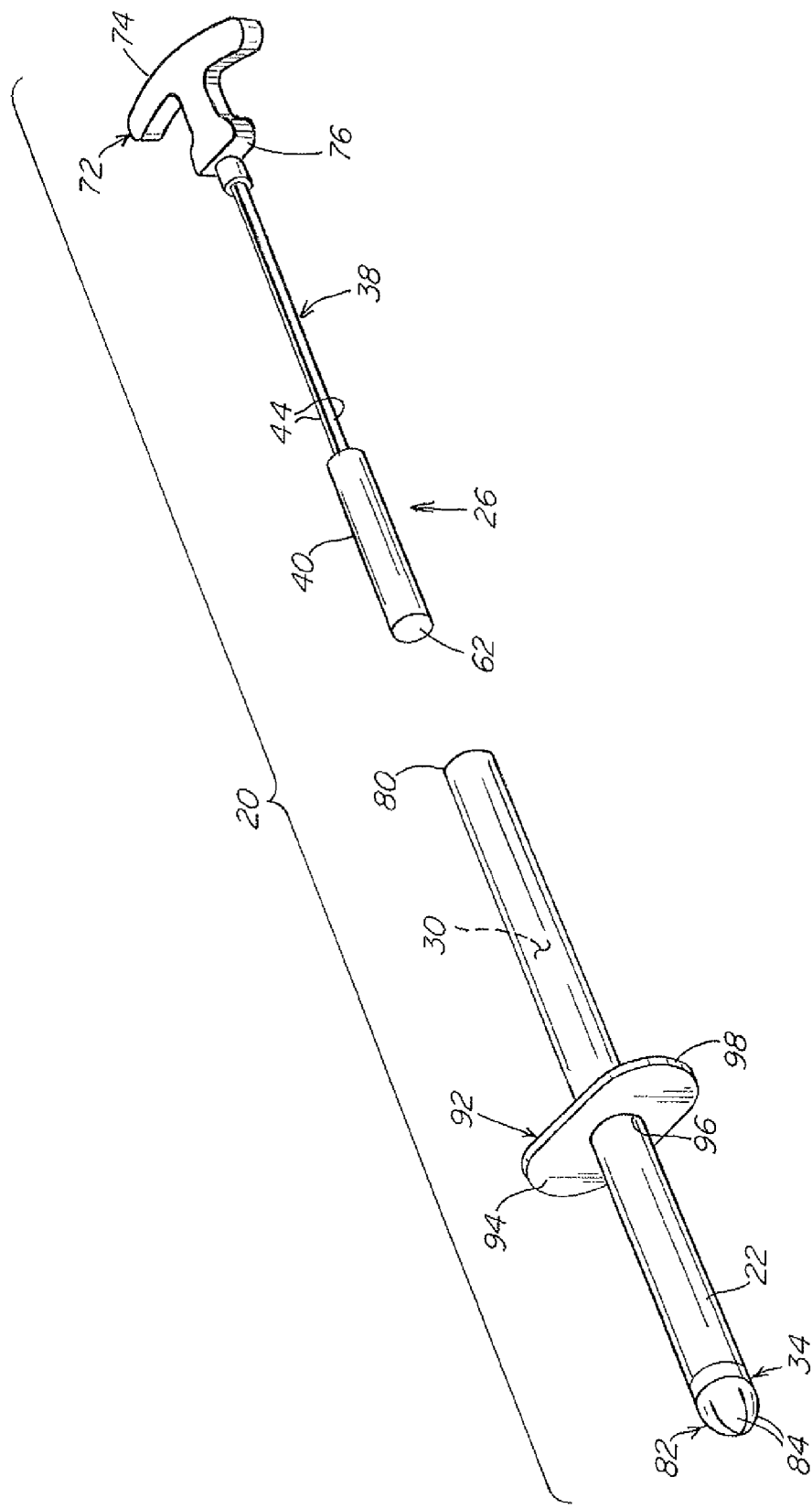
FIG. 2 is an exploded perspective view of the introducer of FIG. 1 in a second configuration.

It may be desirable to combine the loader and the plunger in a single component. In one illustrative embodiment, the introducer 20 may include a dual-purpose component 36 that is configured to be employed as both a loader 24 and a plunger 26. As shown in FIG. 1, the dual-purpose component 36 may be used in a first configuration as a loader 24 to collapse and/or load a prosthetic fabric 28 into a delivery tube 22. As shown in FIG. 2, the dual-purpose component 36 may then be used in a second configuration as a plunger 26 to push the prosthetic fabric 28 through the delivery tube and into the patient. In the illustrative embodiment, the dual-purpose component 36 is reversible between the first and second configurations. However, it is to be appreciated that the introducer may employ separate components for the loader and the plunger, as the present invention is not limited to a reversible dual-purpose component for both the loader and the plunger.

In one illustrative embodiment shown in FIGS. 1 and 3, the dual-purpose component includes a first portion 38 that may be configured to collapse and load the prosthetic fabric 28 into the delivery tube 22 and a second portion 40 that may used as a handle while collapsing and/or loading the fabric 28 when the dual-purpose component 36 is employed as a loader. As shown in FIG. 1, the dual-purpose component 36 may be positioned in a first orientation so that the first portion 38 may be disposed between the second portion 40 and the distal end 34 of the delivery tube to load the prosthetic fabric into the tube in the first or loader configuration. When the dual-purpose component is used as a plunger, it may be positioned in a second orientation so that the second portion 40 may be inserted into the delivery tube to engage and push the collapsed fabric 28 while the first portion 38 may be used to drive the second portion 40 through the tube. As shown in FIG. 2, the second portion 40 may be disposed between the first portion 38 and the distal end 34 of the delivery tube 22 with the first portion extending from the proximal end 32 of the tube in the second or plunger configuration.

As illustrated, the first portion 38 may include a slender, elongated rod that extends in a longitudinal direction from an end of the second portion or loader handle 40. In one embodiment, the loader 24 may be configured to roll the prosthetic fabric 28 about the rod 38 from a first configuration, such as a flat or open configuration, into a rolled configuration that is sized to fit into the lumen 30 of the delivery tube 22. However, it is to be appreciated that the loader may be configured to collapse the fabric 28 about the rod 38 in any suitable manner that reduces the size of the fabric such that it will fit within the lumen 30 of the delivery tube 22. For example, the loader 24 may be configured to fold the fabric 28 into a collapsed configuration.

To facilitate collapsing the fabric, the loader 24 may be configured to grasp or hold onto a portion of the prosthetic fabric 28. In one illustrative embodiment shown in FIG. 5, the rod 38 may include a pair of tines 44 that are spaced apart to form a gap or receptacle 46 therebetween for receiving the fabric 28. A portion of the prosthetic fabric 28 may be inserted between the tines 44 and into the receptacle 46 to help hold and roll the fabric about the rod 38 as it is rotated using the loader handle 40, i.e., the second portion. In one embodiment, the tines are fabricated from a metal material, such as stainless steel, although the tines may be fabricated from any suitable material as would be apparent to one of skill in the art.

It is to be appreciated that the loader 24 may employ other features to hold the prosthetic fabric 28 while it is being collapsed as would be apparent to one of skill in the art. For example, a groove or channel may be formed in a single rod that is configured to receive and hold an edge of the prosthetic fabric 28 as the fabric is rolled about the rod. However, it is to be understood that other embodiments of the loader 24 need not be configured to hold a portion of the fabric 28, as the invention is not limited in this regard.

The tines 44 of the loader may be configured in a manner or include features that facilitate placement of the prosthetic fabric 28 therebetween. In one illustrative embodiment shown in FIG. 5, the free ends 48 of the opposed tines 44 may include a tapered internal surface 50 that forms a gap at the free end of the tines that is wider than at the opposing ends of the tines to facilitate capturing and sliding the prosthetic fabric 28 therebetween. The external surfaces 52 at the distal end 34 of the opposed tines 44 may also be tapered to help with placement about a portion of the fabric 28 or to help with insertion into a delivery tube 22. It is to be appreciated that other embodiments of the loader 24 may include other suitable features to facilitate placing the loader 24 about the fabric 28, while other embodiments may lack such features as the invention is not limited in this manner.

Figure 6:
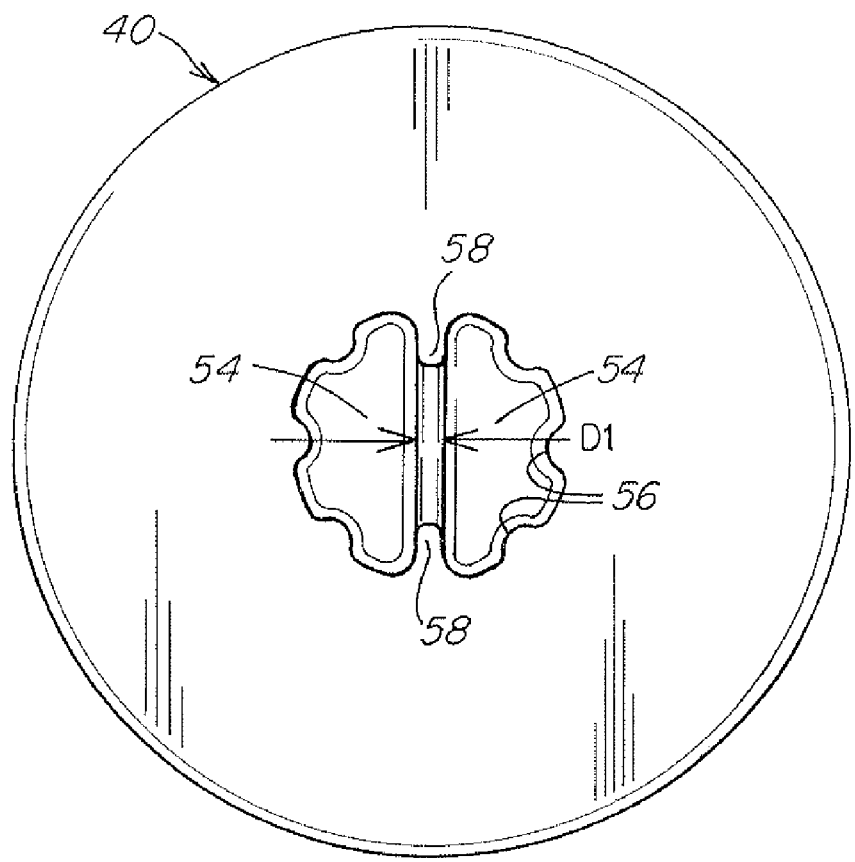
FIG. 6 is an end view of the loader of FIG. 5 taken along section line 6-6 with the first portion of the dual-purpose component removed from view.

In one illustrative embodiment, the rod 38 includes a pair of individual tines 44 that may be secured to the loader handle 40 using any suitable arrangement. In one illustrative embodiment shown in FIG. 6, the loader handle or second portion 40 may be configured to secure the tines using an interference fit. In this regard, the second portion 40 may include a pair of receptacles 54 that are adapted to receive and securely retain the opposed tines 44 therein. As illustrated, each receptacle 54 may include a plurality of projections 56 that are configured to be deformed when the tines 44 are inserted into the receptacle 54, thereby creating an interference fit which retains the tines 44 in the second portion 40. A pair of central projections 58 may separate the receptacles and define a separation distance (D1) between the opposed tines 44, which in turn defines the gap 46 for receiving and retaining a portion of the prosthetic fabric 28. In one embodiment, the separation distance is 0.020 inches. In some embodiments, an adhesive may be used in place of or in conjunction with the projections to secure the opposed tines 44 to the second portion. In this regard, the projections may form gaps within the receptacles for receiving the adhesive. However, it is to be understood that any suitable fastening arrangement may be used to join the tines to the second portion 40, as the invention is not limited in this respect.

In one illustrative embodiment, the first portion 38 of the dual-purpose component 36 may be configured to maintain sufficient space within the lumen 30 of the delivery tube 22 for receiving the collapsed prosthetic fabric 28 when the fabric is collapsed and loaded into the tube 22 using the dual-purpose component 36. The first portion 38 may have a length that is greater than the size of the prosthetic fabric 28 being collapsed and loaded into the delivery tube 22 with the dual-purpose component 36. The second portion 40 of the dual-purpose component may be configured with a diameter that is larger than the first portion 38 to enhance its ability to serve as a loader handle 40 when the dual-purpose component 36 is used as a loader 24. The second portion 40 may also be configured to slide closely within the lumen 30 of the delivery tube 22 when the dual-purpose component 36 is used as a plunger 26. The second portion may have a length that is shorter than the first portion 38. In one embodiment, the dual-purpose component has an overall length of 13.5 inches and the second portion has a length of 3.0 inches. In another embodiment, the dual-purpose component has an overall length of 10.0 inches and the second portion has a length of 3.0 inches. In one embodiment, the first portion has a diameter of 0.19 inches and the second portion has an outer diameter of 0.77 inches which is adapted for use with a delivery tube having an inner diameter of 0.78 inches. In another embodiment, the first portion has a 0.15 inch diameter and the second portion has an outer diameter of 0.59 inches which is adapted for use with a delivery tube having an inner diameter of 0.60 inches. However, it is to be understood that the first and second portions of the dual-purpose component may have any suitable configurations and sizes apparent to one of skill in the art to accommodate repair fabric of various shapes and sizes, as the invention is not limited in this respect.

As indicated above, when employed as a plunger 26, the second portion 40 of the dual-purpose component may be inserted into the lumen 30 of the delivery tube 22 and used as a plunger head 40 to push the collapsed prosthetic fabric 28 through the tube 22. In one illustrative embodiment, the second portion or plunger head 40 may be configured to conform closely with the inner diameter of the delivery tube 22. In this manner, the fit between the plunger head 40 and the delivery tube 22 guides the plunger 26 through the lumen of the tube to deliver prosthetic fabric 28 without causing excessive resistance between the plunger 26 and the delivery tube 22. As illustrated, the second portion 40 or plunger head may have a cylindrical shape that conforms to the tubular shape of the delivery tube 22. The distal end 62 of the plunger head may have a substantially flat surface 62 that is adapted to contact the prosthetic fabric 28 and deliver it through the distal end of the tube 22.

It is to be appreciated that the plunger head 40 may have any suitable configuration apparent to one of skill for sliding within the lumen 30 to push the prosthetic fabric through the delivery tube. For example, in some embodiments, the contact surface 62 of the plunger head 40 may have a concave shape that directs the prosthetic fabric 28 toward a central portion of the lumen 30 when the fabric 28 is being pushed through the tube. In other embodiments, the plunger head 40 may have a cross section that is substantially smaller than the cross section of the lumen 30. In such embodiments, the plunger 26 may be used to press the prosthetic fabric 28 through the lumen 30 by selectively contacting points of the collapsed prosthesis loaded in the delivery tube 22.

The second portion 40 of the dual-purpose component 36, whether employed as a loader handle or a plunger head, may be fabricated from any suitable material using any suitable manufacturing processes apparent to one of skill in the art. In one illustrative embodiment shown in FIGS. 1-4, the second portion 40 may have a solid cylindrical shape that may be extruded from a plastic material, such as a polycarbonate. However, it may be desirable to reduce the amount of material used for the second portion. In another illustrative embodiment shown in FIG. 5, the second portion 40 may be injection molded from a plastic material, such as an acrylic monomer (e.g., CYROLITE), into a configuration that is lighter and uses less material than a solid component. As illustrated, the second portion 40 may include a plurality of ribs 66 and cavities 68 that reduce the weight of the part while maintaining its structural integrity. The ribs 66 may also assist with the molding process by preventing uneven cooling of the plastic. To provide structure, the second portion 40 may be formed with three solid rings 70, including a ring at each end of the body and an intermediate ring provided in the middle portion of the body. These rings 70 may enhance the overall structure of the second portion 40 and provide a relatively close fit to the inner surface of the delivery tube 22.

To facilitate delivery of the prosthetic fabric 28 from the delivery tube 22, it may be desirable to provide the plunger 26 with a handle 72 or other feature that allows a user to efficiently exert a force on the end of the plunger 26 to expel the fabric 28 from the tube 22. In one illustrative embodiment shown in FIGS. 2 and 4, a handle 72 may be attachable to the free end of the first portion of the dual-purpose component 36 when it is employed in the second configuration as a plunger 26. To enhance use of the dual-purpose component 36 as both the loader 24 and the plunger 26, the handle 72 may be configured to be readily attached to and removed from the ends 48 of the tines 44 depending on the particular application of the dual-purpose component 36. In one embodiment, the handle 72 may be configured with a tapered receptacle that allows the handle to be slipped on and off the tines 44.

The handle 72 may include an ergonomic surface 74 that is adapted to be grasped by the surgeon. As illustrated, the ergonomic surface 74 may have a larger surface area in a direction orthogonal to the plunging direction, and in this manner, reduces the pressure that the user feels when depressing the plunger 26 through the tube 22.

It is to be understood that a handle 72 is not required in all embodiments of the invention, and that other handle configurations may be used to assist the user in expelling the fabric 28 from the tube 22 with the plunger 26. For example, a handle may include a cylindrical sheath that is slipped over the opposed tines 44 of the dual-purpose component 36 when used in a second configuration as a plunger. It is also to be understood that, in other embodiments, the handle may be permanently attached to the plunger rather than using a removable component, as the invention is not limited in this regard.

It may be desirable to limit the travel of the plunger 26 through the delivery tube 22, for example, to indicate to a surgeon when the plunger 26 has traveled a sufficient distance to deliver a prosthetic fabric 28 into a patient. In this regard, the introducer 20 may be provided with a stop 76 that is configured to limit travel of the plunger a predetermined distance through the delivery tube.

In one illustrative embodiment, the introducer may include a stop that prevents travel of the plunger 26 beyond a desired distance through the delivery tube 22. As illustrated in FIG. 4, the stop 76 may include a portion 78 of the plunger handle 72 that is configured to contact the proximal end 80 of the delivery tube 22 to limit further movement of the plunger 26 through the tube. In one embodiment, the stop may be configured to limit movement of the plunger 26 so that the distal end 38 of the plunger head 40 does not extend beyond the distal end 34 of the delivery tube 22.

It is to be appreciated that any suitable stop may be employed with the introducer 20 and/or the stop 76 may be configured to allow any desired amount of travel of the plunger 26 within the delivery tube 22 as would be apparent to one of skill in the art. For example, the stop may be configured to allow the plunger 40 head to extend a predetermined distance beyond the distal end of the delivery tube 22.

The distal end 34 of the delivery tube 22 may be configured to facilitate insertion of the tube 22 through an incision 100 or naturally occurring orifice into the patient. In one illustrative embodiment shown in FIG. 7, the distal end 34 may have a hemispherical shape that may ease insertion of the tube 22 through an incision 100 or orifice. It is to be understood that other features and/or shapes may be used to facilitate insertion of the delivery tube 22 into and/or through an incision 100, as would be apparent to one of skill in the art. For example, other embodiments may employ a distal end 34 having any suitable rounded or tapered shape for inserting the tube into the patient. Although it may be desirable to provide a distal end 34 that is configured to ease insertion of the tube 22 into a patient, it is to be appreciated that not all embodiments of the invention are limited in this manner.

In some surgical procedures, it may be desirable to at least partially obstruct the lumen 30 of the delivery tube 22. For example, it may be desirable to reduce the potential entry of tissue and other debris into the lumen 30 as the delivery tube is inserted into a patient. During laparoscopic procedures, it may be desirable to reduce potential leakage through the delivery tube to maintain a positive pressure inside an internal body cavity, such as the peritoneal cavity during hernia repair surgery.

Figure 7:
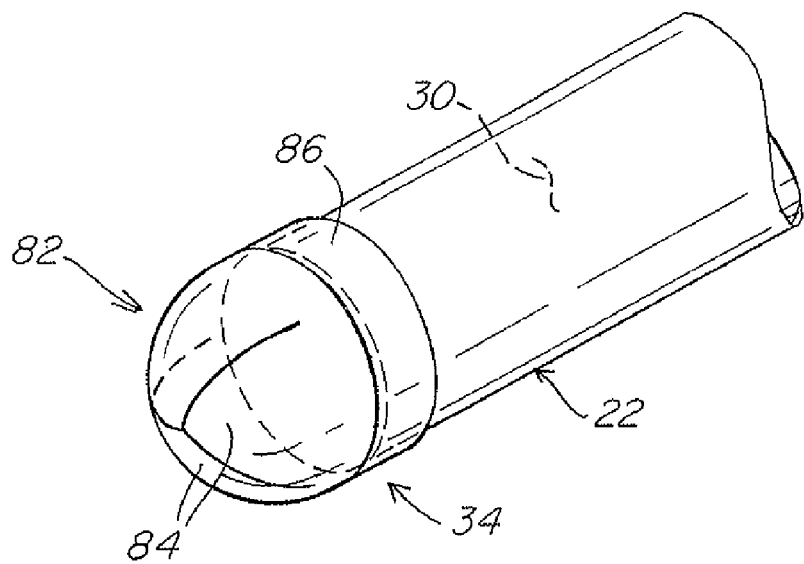
FIG. 7 is a perspective view of a closure at the distal end of the delivery tube according to one illustrative embodiment of the invention.
Figure 15:
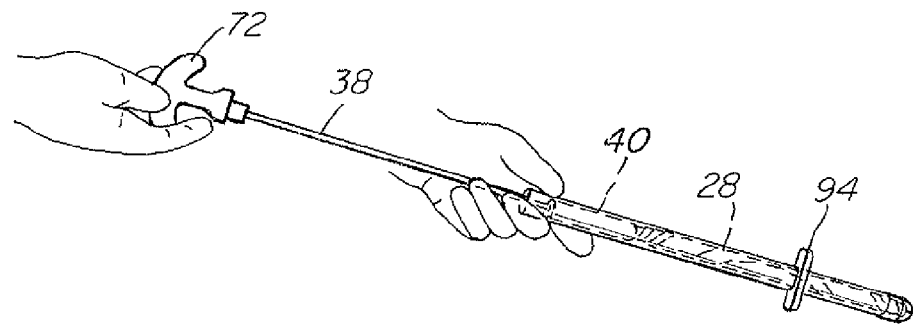

In one illustrative embodiment shown in FIGS. 7 and 15, the delivery tube 22 may include a valve or closure 82 that is operable between a closed position and an open position. In the closed position, the closure acts to sufficiently obstruct the lumen 30 of the delivery tube 22 so as to reduce the potential entry of tissue and other debris into the lumen and/or to reduce potential leakage of a gas through the delivery tube to maintain a positive pressure inside an internal body cavity during a laparoscopic procedure. In the open position, the closure allows passage of the prosthetic fabric 28 from the lumen 30. As illustrated, the closure 82 may be provided at the distal end 34 of the delivery tube 22. However, it is to be understood that the closure may be provided at any suitable location on the delivery tube as would be apparent to one of skill in the art.

The closure may include a plurality of flaps 84 that are movably supported at the distal end 34 of the delivery tube 22. In one illustrative embodiment, the closure 82 may include three flaps 84 that extend inwardly from the periphery of the tube 22 toward the center of the lumen 30 in the closed position of the closure 82. Each flap 84 may be configured to have a generally triangular shape of equal size so that the flaps 84 combine to close off the end of the delivery tube 22 when the flaps 84 are in the closed position. As illustrated, each of the flaps 84 may be rounded so that the closure 82 has a hemispherical shape in the closed position to facilitate insertion of the delivery tube 22 into a patient. It is to be appreciated that not all embodiments are limited to the illustrative embodiment as the closure may include any number of flaps 84, including one or more flaps, that are configured in any suitable shape as would be apparent to one of skill in the art.

The closure 82 may be operable between the closed and open positions in response to a force applied to it by the prosthetic fabric 28. In one illustrative embodiment, as the prosthetic fabric 28 is being expelled from the tube 22, the fabric 24 pushes against the closure causing it to move to the open position and allow passage of the fabric 28 therethrough. Upon depressing the plunger 26, the fabric 28 is pushed through the delivery tube 22 until it contacts an interior surface of the closure 82. Continued application of force to the plunger 26 is then transferred through the prosthetic fabric 28 and onto the interior surface of the closure 82, causing the closure 82 to move from the closed position to the open position to allow passage of the fabric 28 from the lumen 30. It is to be understood that the closure may be configured to operate in other ways. For example, the closure may employ any suitable mechanism as would be apparent to one of skill in the art that allows a user to actuate the closure between the open and closed positions as desired.

In one illustrative embodiment, the closure 82, including the flaps 84, may be fabricated as an integral device from a flexible material that facilitates operation between the closed and an open positions. In one embodiment, the closure 82 may be fabricated from a flexible plastic, such as polyvinyl chloride (PVC) having a durometer of 80-85, Shore A scale, and a thickness of approximately 0.03 inches that allows the flaps 84 to flex between the closed position and the open position. However, it is to be appreciated that the fabrication of the closure 82 is not limited to a flexible material. In this regard, the flaps 84 may be fabricated from a relatively rigid material that is connected to the delivery tube 22 in a manner that allows the flaps to move between the closed and open positions. For example, the closure may include relatively rigid flaps that are connected to the tube using a mechanical hinge or a living hinge as would be apparent to one of skill in the art.

The closure 82 may be fabricated integral with the delivery tube or as a separate component that is attachable to the delivery tube 22. In one illustrative embodiment, the closure 82 may include a body portion 86 with the flaps 84 supported at one end thereof. The body portion 86 may have a tubular shape that is configured to slide over the distal end 34 of the delivery tube 22. The closure may be secured to the delivery tube 22 with an adhesive or other suitable fastener. In another embodiment, the closure 82 may be configured to be secured to the delivery tube 22 with an interference fit such that no adhesive or fastener is necessary, as the present invention is not limited in this respect.

In one embodiment, the body portion 86 has an inner diameter 0.82 inches and is capable of mating with a delivery tube 22 that has an outer diameter of 0.84 inches. In another embodiment, the body portion 86 has an inner diameter of 0.64 inches and is capable of mating with a tube 22 that has an outer diameter of 0.66 inches.

As indicated above, in some laparoscopic procedures, it may be desirable to maintain a positive pressure inside of an internal body cavity, such as the peritoneal cavity during hernia repair surgery. In some embodiments, the loaded prosthetic fabric itself may reduce the flow of gases through the delivery tube. In other illustrative embodiments, the introducer 20 may include one or more features to reduce the flow of gases from the internal cavity during a surgical procedure. In one embodiment, the closure 82 may be configured to significantly reduce or substantially limit gas flow through the delivery tube 22 when in its closed position. However, it is to be appreciated that the closure 82 may allow some passage of gases when in the closed position, as the present invention is not limited to eliminating, or even to restricting, the passage of a gas through the delivery tube 22.

If desired, the introducer 20 may include other features in addition to or in place of the closure 82 to limit the passage of gases from an internal cavity during a surgical procedure. In one illustrative embodiment, the plunger head 40 may be configured to closely conform to the inner surface of the delivery tube 22 so as to limit the escape of gases through the delivery tube 22. More particularly, the plunger head 40 may be sized to conform substantially to the wall of the tube, leaving a gap that is large enough to allow the plunger head 40 to readily slide within the lumen 30, while allowing minimal passage of gases between the plunger head 40 and tube wall.

In one embodiment, the inner diameter of the delivery tube is approximately 0.78 inches and the plunger head has an outer diameter of approximately 0.77 inches. In another embodiment, the inner diameter of the delivery tube 22 is approximately 0.60 inches and the outer diameter of the plunger head 40 is approximately 0.59 inches. To further reduce gas leakage past the plunger head 40, a seal, such as an o-ring, may be disposed about the plunger head 40 to engage against the inner wall of the tube 22. However, it is to be appreciated that the present invention is not limited in this regard, as the introducer 20 may be configured without any features for limiting the passage of gases from an internal cavity of a patient.

It is to be appreciated that the prosthetic fabric 28 may be fabricated from one or more materials that exhibit a relatively high surface adhesion or tension with the delivery tube 22. Such surface adhesion between the prosthetic fabric 28 and the delivery tube 22 may make it more difficult than would otherwise be desired to move the fabric 28 through the lumen 30, such as when loading the fabric 28 into the delivery tube 22 or when pushing the fabric 28 through the tube 22. Thus, it may be desirable to provide the introducer 20 with one or more features to facilitate easy passage of the prosthetic fabric 28 through the delivery tube 22.

Figure 8:
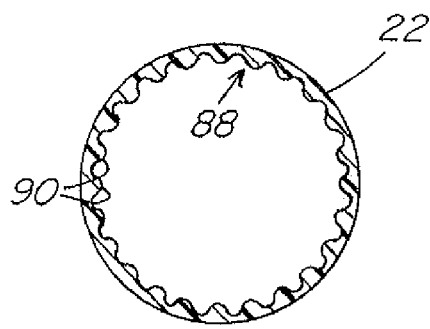
FIG. 8 is a cross-sectional view of the delivery tube of FIG. 1 taken along section line 8-8.

In one illustrative embodiment shown in FIG. 8, the delivery tube may be provided with a textured internal surface 88 that is configured to reduce the surface contact area, as compared to a smooth internal surface, between the tube 22 and the prosthetic fabric 28 loaded in the tube 22. The textured surface 88 may include a plurality of protrusions 90 that present a contact area that is to be engaged by the fabric 28. By reducing the contact area between the fabric 28 and the tube 22, the surface adhesion between the prosthetic fabric 28 and the tube 28 may be similarly reduced so that the fabric 28 may be more readily passed through the tube 22.

In one embodiment, the protrusions may include a plurality of serrations or ribs 90 that are disposed about the inner circumference of and extend along the length of the tube 22 in an end-to-end direction to facilitate ease of delivery of the prosthetic fabric. As shown, the ribs 90 may be configured to form an undulating, inner surface of the delivery tube 22 that significantly reduces the effective surface area of the tube 22 that is engaged by the fabric 28. In one embodiment, the serrations or ribs 90 have an average height of approximately 0.001 to 0.002 inches and, depending on the size of the tube, between 250 and 350 ribs are arranged about the inner surface of the delivery tube 22 so as to reduce the effective contact area with the prosthetic fabric 28 to approximately 10% of the surface area of a non-textured inner surface. It is to be appreciated that the tube 22 may employ any number of serrations or ribs 90 having any suitable size apparent to one of skill to provide any desired reduction in surface contact area. It is also to be understood that the textured surface 88 is not limited to ribs 90 that are formed by an undulating surface that presents a rounded contact point. In other embodiments, the ribs may be configured with pointed, flat or other shaped contact points. It should also be understood that the ribs 90 may be oriented in other directions as would be apparent to one of skill in the art. For example, the ribs may extend in a helical or any other suitable arrangement. It is also to be appreciated that the textured surface 88 is not limited to serrations or ribs 90, as any suitably configured protrusions may be provided on the inner surface to reduce the effective contact area between the tube 22 and the fabric 28.

In one illustrative embodiment, the ribs 90 may be integrally formed with the delivery tube 22 during an extrusion process. In this regard, longitudinal serrations may be formed in the extrusion die. However, it is to be understood that the ribs 90, or other suitable protrusion configurations that form a textured surface 88, may be formed or applied to the delivery tube 22 in any other suitable manner apparent to one of skill, as the invention is not limited in this respect. For example, in other to embodiments, the textured surface 88 may be formed on the inner surface of the delivery tube 22 by grit blasting or other suitable surface treatment.

Figure 9:
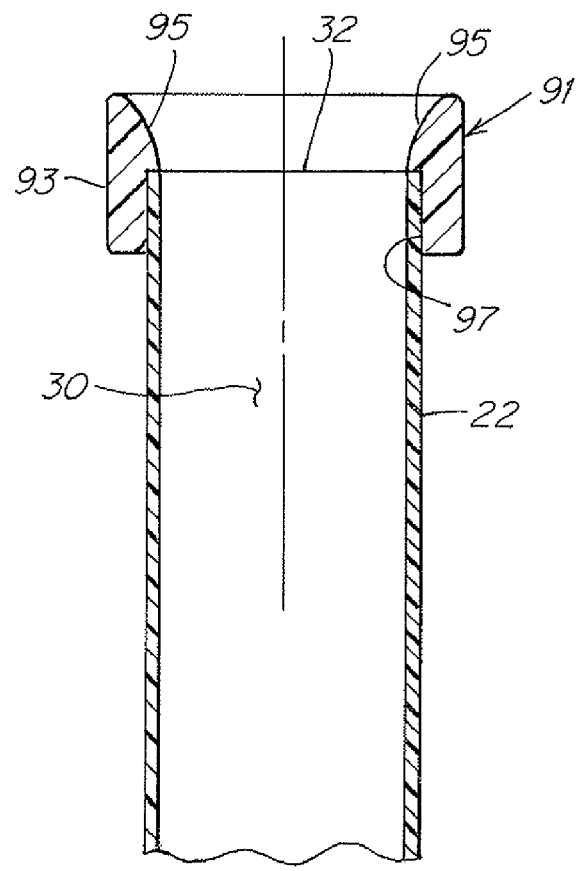
FIG. 9 is a cross-sectional view of a guide at the proximal end of the delivery tube according to one illustrative embodiment of the invention.

To facilitate insertion of the prosthetic fabric into the delivery tube, it may be desirable to provide a guide at the proximal end of the tube that is configured to direct the fabric into the lumen. In one illustrative embodiment shown in FIG. 9, the introducer 20 includes a guide 91 at the proximal end 32 of the delivery tube 22. The guide may include a body 93 with a guide surface 95 that is sloped or angled to direct the fabric into the lumen 30 of the tube as the fabric is inserted into the end of the tube. As illustrated, the guide surface 95 may have a generally frusto-conical shape that forms a funnel-like guide into the lumen. The guide surface 95 may be curved in the longitudinal direction.

In one embodiment, the guide surface defines an opening that decreases from a diameter of approximately 1.04 inches at its proximal end to a diameter of approximately 0.78 inches at its distal end at the entrance to the lumen. In another embodiment, the guide surface defines an opening that decreases from a diameter of approximately 0.87 inches at its proximal end to a diameter of approximately 0.60 inches at its distal end at the entrance to the lumen. It is to be understood that the guide may employ a guide surface having any suitable shape or size to facilitate insertion of the fabric into the tube as would be apparent to one of skill in the art.

The guide may be a separately formed component that is mounted to the proximal end of the tube. As illustrated, the body 93 may include a counterbore 97 that is configured to receive the end of the tube. The body may be attached to the tube using any suitable arrangement apparent to one of skill in the art. In one embodiment, the guide may be secured to the tube using a suitable adhesive. Other examples may include, but are not limited to, an interference fit, a threaded connection and ultrasonic welding. In one embodiment, the guide may be molded from a plastic material, such as an acrylic monomer (e.g., CYROLITE). However, it is to be appreciated that the guide may be fabricated using any suitable process from any suitable material apparent to one of skill in the art.

Rather than being fabricated as a separate component, the guide 91 may be integrally formed on the proximal end of the tube. In one embodiment, the guide may be thermo-formed on the end of the tube by heating and expanding the softened tube material over a mandrel having the desired shape for the guide. In another embodiment, the end of the tube may be subjected to a radio frequency (RF) forming process which softens the tube material as it is being moved over a shaped mandrel to form the guide. It is to be understood that the guide may be integrally formed on the tube employing any suitable process apparent to one of skill in the art.

A surgeon may consider it desirable to limit the penetration depth of the introducer 20 into the patient during a surgical procedure. In this regard, the introducer 20 may be provided with a suitable stop 92 that is configured to engage the patient upon a predetermined amount of insertion of the introducer 20. In one illustrative embodiment shown in FIGS. 1-4, the introducer 20 includes a stop 92 that is disposed on the delivery tube 22 at a desired distance from the distal end 34 of the tube 22 corresponding to the maximum desired insertion depth of the introducer 20. As illustrated, the stop 92 may include a flange 94 that is disposed on an external surface of the delivery tube 22. The flange 94 may be configured to contact an area adjacent to an incision in a patient through which the introducer 20 is inserted into the patient to prevent further insertion when a desired insertion depth is reached by the delivery tube 22.

As is to be appreciated, it may be desirable in some applications to adjust the insertion depth of the delivery tube 22 for different size patients or different types of surgical procedures. In one illustrative embodiment, the flange 94 may be adjusted along the length of the delivery tube 22 so that a user may selectively position the flange 94 relative to the distal end 34 of the delivery tube 22 to set a desired amount of insertion depth. For example, the flange 94 may be adjusted from one position set at a first distance from the distal end 34 of the delivery tube 22, to a second position set at a second distance from the distal end 34 of the delivery tube 22. The flange 94 may be configured to be moved to an infinite number of different locations, or a finite number of indexed locations along the delivery tube 22. In other embodiments, insertion depth may be varied in other ways. For instance, some embodiments may have indicia on the outer surface of the delivery tube 22 to assist a surgeon in limiting the insertion depth, as the present invention is not limited in this regard.

In one illustrative embodiment, the flange 94 may be slidably mounted to the delivery tube 22 to allow a user to readily adjust the insertion depth of the introducer 20. The flange 94 may be mounted on the delivery tube 22 using an interference fit so that the flange 94 maintains its position along the delivery tube 22 until it is repositioned by a user, when desired, to adjust the insertion depth. In one embodiment, the flange 94 may be fabricated from a soft elastomeric material, such as a urethane having a durometer of 70-75, Shore A scale, and a thickness of approximately 0.125 inches. The flange 94 may have an aperture 96 with a diameter of approximately 0.816 inches for mating with a delivery tube 22 having an outer diameter of approximately 0.840 inches. In another embodiment, the flange 94 may be provided with an aperture 96 having a diameter of approximately 0.635 inches to mate with a tube 22 having an outer diameter of approximately 0.660 inches. The flange 94 may be repositioned along the delivery tube 22 by applying an amount of force needed to overcome the retention force between the flange 94 and the tube created by the interference fit. However, it is to be appreciated that the flange 94 need not be movable and may be permanently affixed to the delivery tube 22 at a predetermined distance from the distal end 34 of the tube 22. It is also to be understood that other embodiments may not include a flange 94 or any other feature for limiting insertion depth of the tube 22 into the patient, as the invention is not limited in this regard.

For some applications, the delivery tube 22 may include a feature which can be grasped with one hand while a surgeon depresses the plunger 26 with the other hand. In one illustrative embodiment, the flange 94 may be configured to be grasped in such a manner. However, it is to be appreciated that any suitable gripping feature apparent to one of skill in the art may be employed with the introducer. For example, an ergonomic gripping surface may be disposed about the delivery tube 22 at a position proximal to the flange 94.

In the illustrative embodiment described above, the delivery tube 22 has a tubular configuration, such that it may be desirable to provide the introducer 20 with one or more features configured to reduce the likelihood that the introducer 20 will roll or otherwise move when it is lying on a flat or sloped surface. In one illustrative embodiment, the flange 94 may be configured with a non-circular shape that, when placed against a flat and/or sloped surface, reduces the potential for the introducer 20 to roll across the surface. As illustrated, the outer periphery 98 of the flange 94 may have a generally rectangular shape with straight parallel sides and rounded corners. In one embodiment, the outer periphery 98 has a length of approximately 2.3 inches and a width of approximately 1.4 inches. However, it is to be understood that the flange 94 may be configured with other non-circular shapes, including rectangular, square, triangular, oval and elliptical shapes, as would be apparent to one of skill in the art to reduce the potential for the introducer 20 to roll when placed on a flat or sloped surface, as the invention is not limited in this regard.

In one illustrative embodiment, the delivery tube 22 may have a length sized to fully enclose the collapsed prosthetic fabric 28 for subsequent delivery into the patient. As illustrated in FIGS. 2 and 4, the delivery tube 22 may have a length adequate to enclose the entire prosthetic mesh 28 when rolled and placed into a lumen 30 of the delivery tube 22. In one embodiment, the delivery tube 22 is approximately 13.5 inches long. In another embodiment, the delivery tube 22 is approximately 10.0 inches long. However, not all embodiments of the invention are constructed in this manner, as some may be sized substantially longer than a collapsed prosthetic fabric 28, and others may not be sized to fully enclose a prosthetic fabric 28 as the invention is not limited in this respect.

It may be desirable for a user to inspect the collapsed prosthetic fabric 28 after it has been loaded into the delivery tube 22. In one illustrative embodiment, the delivery tube 22 may be fabricated from a translucent or transparent material that allows a user to readily view the contents of the delivery tube 22. In one embodiment, the delivery tube 22 may be made from a transparent or translucent plastic material, such as a polycarbonate (e.g., MAKROLON). Rather than forming the entire tube from a transparent or translucent material, other embodiments may include a transparent or translucent window along some portion of the tube that provides a view at one or more discrete points. However, it is to be appreciated that the delivery tube may be made entirely of an opaque material, as the present invention is not limited to include translucent or transparent materials.

One illustrative embodiment of a method of delivering a prosthetic fabric using the introducer 20, and the various components of the introducer 20, will now be described with reference to FIGS. 10-19.

Figure 10:
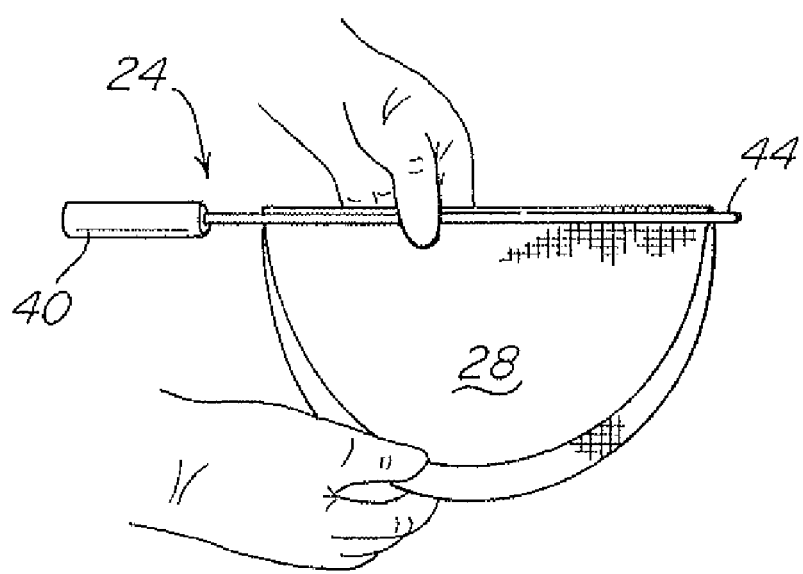
FIGS. 10-16 illustrate a method of delivering a prosthetic fabric into a patient using the delivery tube of FIGS. 1-4 according to one embodiment of the invention.
Figure 11:
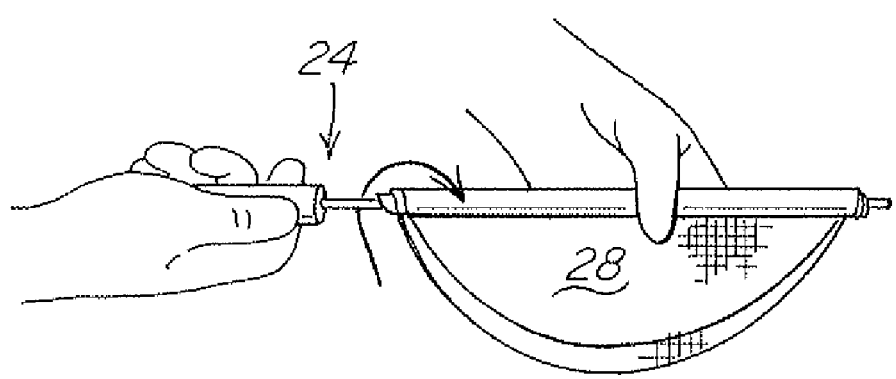

As shown in FIG. 10, a portion of a prosthetic fabric 28 may be placed between the opposed tines 44 of the loader 24 using the dual-purpose component 36 in its first configuration. With the fabric 28 placed between the tines, a user grasps the loader handle 40 (the second portion of the dual-purpose component) with one hand and places the other hand about the fabric 28 as shown in FIG. 11. The loader 24 may then be rotated either clockwise or counterclockwise, as desired by the user, to collapse the fabric 28 into a rolled configuration.

Figure 12:
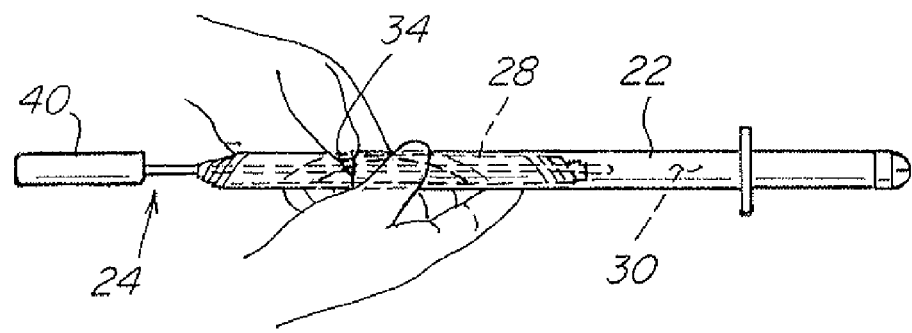
Figure 13:
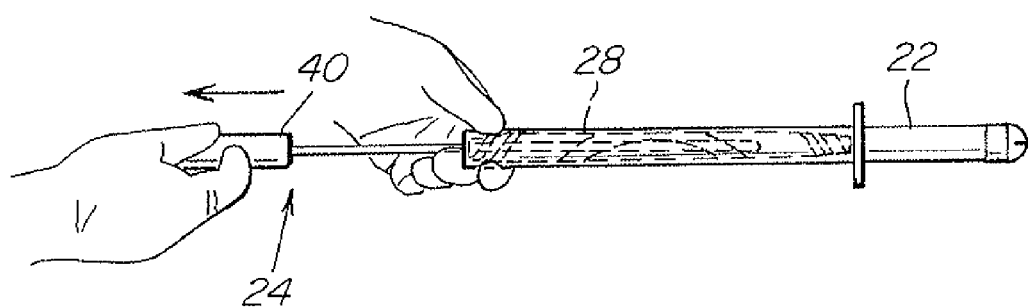

As shown in FIG. 12, the collapsed fabric 28 may then be inserted through the proximal end 34 of the delivery tube 22 and into the lumen 30 using the dual-purpose component in a first orientation. With the collapsed fabric 28 loaded into the delivery tube 22, the loader 24 may then be retracted from the delivery tube while maintaining the prosthetic fabric 28 within the lumen, as shown in FIG. 13. The fabric 28 may be maintained in the tube 22 by placing the thumb, a finger or other portion of the user's hand over the proximal end of the tube as the loader 24 is being retracted from the tube 22. In other embodiments, the fabric may be maintained in the delivery tube by squeezing or deforming a portion of the tube at or near the proximal end as the loader is being retracted from the tube.

Figure 14:
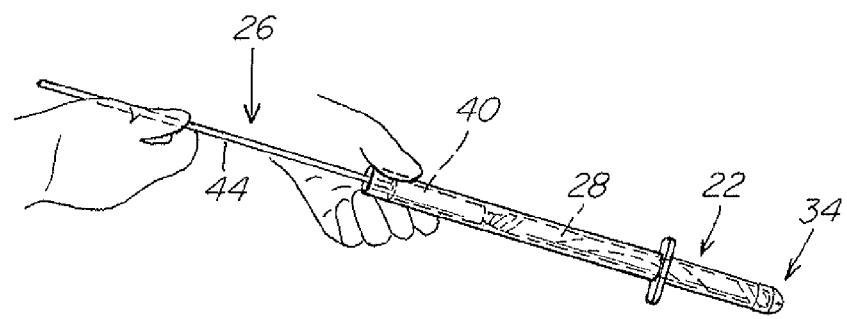
Figure 16:
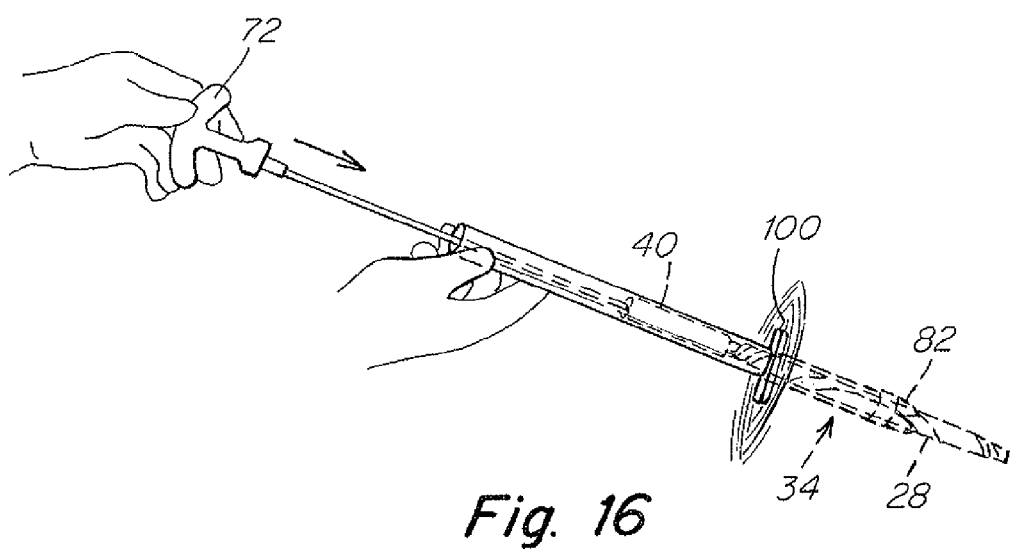

As shown in FIG. 14, once retracted from the tube 22, the dual-purpose component 36 may be reversed to a second orientation so that it may be used in a second configuration as a plunger 26. In this orientation, the plunger head 40 (second portion of the dual-purpose component 36) may be inserted into the delivery tube 22 with the tines 44 extending from the proximal end 32 of the tube 22 in a direction away from the distal end 34 of the tube 22. The plunger handle 72 may be placed on the free ends 48 of the tines 44, as shown in FIG. 15. The delivery tube may then be inserted through an incision 100 and into the patient, as shown in FIG. 16. The plunger 26 may then be depressed by the user, when desired, to expel the collapsed prosthetic fabric 28 from the delivery tube 22 and into the patient.

It is to be appreciated that the foregoing method represents one possible way of delivering a prosthetic fabric into a patient using the introducer 20. In this regard, it is to be understood that the method may employ one or more different acts as would be apparent to one of skill in the art. For example, rather than loading the collapsed fabric 28 into the delivery tube 22 using the loader 24, the collapsed fabric may first be removed from the loader 24 and then subsequently inserted into the delivery tube 22 without use of the loader 24. In another embodiment, a separate loader 24 and plunger 26 may be employed instead of the dual-purpose component.

During particular surgical procedures, such as a laparoscopic procedure, it may be desirable to employ a device to facilitate insertion of the introducer into the patient. For example, during a laparoscopic procedure, it may be necessary to remove a laparoscopic cannula 102 from an incision 100 in the patient to allow insertion of the introducer 20 through the same incision 100. To retain a pathway through the incision 100, a device, such as a switching stick 104, may be placed through the incision prior to removal of the cannula 102. The switching stick 104 may then be used to guide the introducer through the incision 100 and into the patient. Once the prosthetic fabric 28 is delivered with the introducer 20, the switching stick 104 may then be used to reintroduce the cannula 102 into the patient through the incision.

One illustrative embodiment of a method of inserting the introducer 20 using a switching stick 104 will now be described with reference to FIGS. 17-19.

Figure 17:
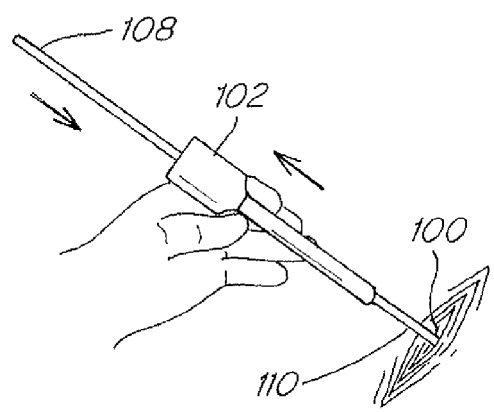
FIGS. 17-19 illustrate a method of replacing laparoscopic instruments in the incision of a patient using a switching stick according to one embodiment of invention.

As shown in FIG. 17, the switching stick 104 may be inserted through a cannula 102, or other laparoscopic device, previously placed through an incision in the patient. Once the switching stick 104 has been inserted, the cannula 102 may be withdrawn over the switching stick and removed from the incision.

Figure 18:
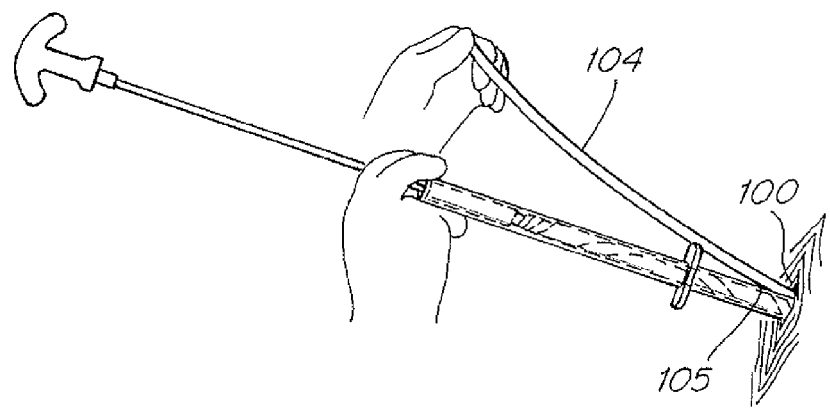

As shown in FIG. 18, with the switching stick 104 in place, the introducer may be inserted through the incision 100 and into the patient using the switching stick 104 as a guide. In this regard, the outer surface 105 of the delivery tube 22 may be placed against and slid along the switching stick 104 to facilitate insertion of the introducer 20 in a shoehorn-like manner. Once the prosthetic fabric 28 is delivered to the patient, the introducer may be removed from the incision 100 while maintaining the switching stick 104 in the incision.

Figure 19:
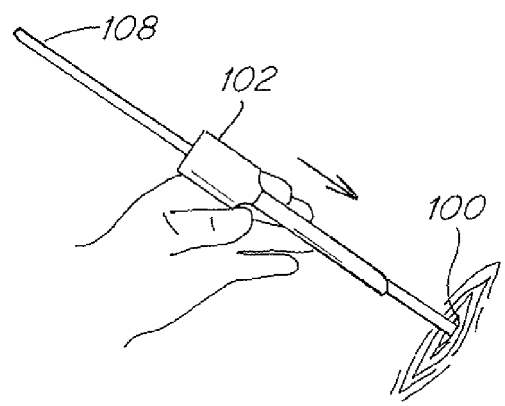

As shown in FIG. 19, the cannula, or another laparoscopic instrument, may then be placed over the switching stick 104 and inserted through the incision 100 and into the patient. The switching stick 104 may then be withdrawn from the cannula 102 and removed from the patient.

In one illustrative embodiment, the switching stick 104 may include an elongated body 106 that is configured to be readily inserted through a laparoscopic instrument, such as a cannula 102. Preferably, the switching stick 104 has a length that is longer than conventional laparoscopic hardware, such as a cannula, that is placed directly into an incision 100 during a laparoscopic procedure. This allows a surgeon to grasp the proximal end 108 of the switching stick 104 while the cannula 102 is removed from the incision 100 until the distal end of the cannula is removed, thereby exposing a distal portion 110 of the switching stick 104. The surgeon may then grasp the switching stick 104 at its exposed distal portion 110 and release the grip on the proximal portion 108 so that the cannula 102 may be removed while retaining the stick 104 in the incision 100. In one embodiment, the switching stick 104 has a length of approximately 16 inches, although the switching stick 104 may be configured to have any suitable length apparent to one of skill in the art.

To facilitate insertion of the introducer 20, it may be desirable to configure the switching stick 104 to act as a guide. In this manner, with the switching stick 104 located in the incision 100, the introducer or other laparoscopic instrument may be slid along a surface of the switching stick and into the incision 100.

Figure 20:
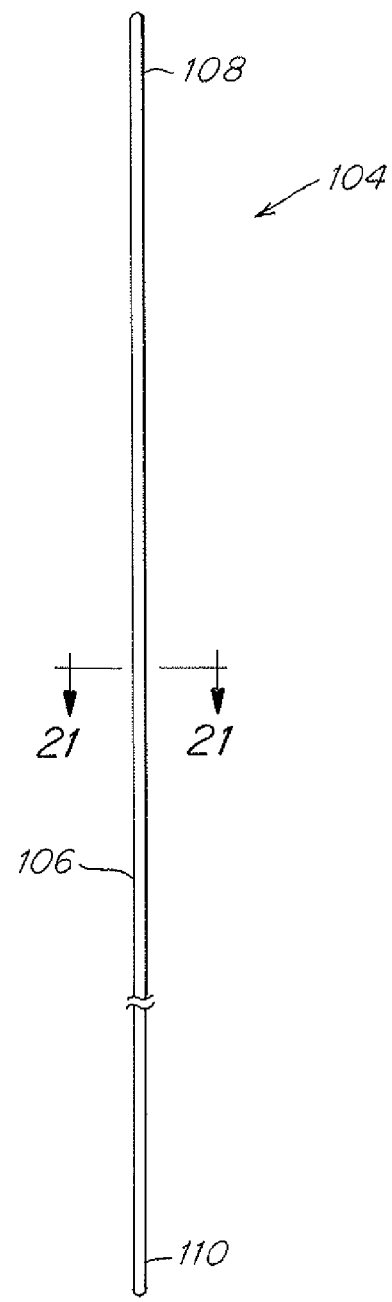
FIG. 20 is a side view of a switching stick according to one illustrative embodiment of the invention.
Figure 21:
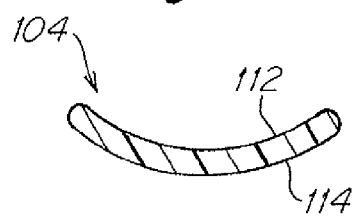
FIG. 21 is a cross-sectional view of the switching stick of FIG. 20 taken along section line 21-21.

In one illustrative embodiment shown in FIGS. 20-21, the body of the switching stick may have a curved shape that helps guide the delivery tube 22 of the introducer 20 into an incision 100. As shown, the switching stick 104 may have an inner surface 112 with a concave shape and an outer surface 114 with a convex shape. The inner surface 112 may be configured to conform to the shape of the delivery tube 22. In one embodiment, the inner surface 112 has a radius of curvature of approximately 0.32 inches and the outer surface 114 has a radius of curvature of approximately of 0.40 inches. However, it is to be understood that the switching stick 104 may be configured to have any shape apparent to one of skill in the art for guiding any laparoscopic instrument into an incision 100. For example, a switching stick 104 having substantially flat cross section or a circular cross section may also be used to facilitate insertion of various instruments. In one embodiment, the switching stick has a maximum cross sectional dimension of 0.395 inches, although the invention is not limited in this respect as other sizes may be used.

The body 106 of the switching stick 104 may be relatively flexible to allow a user to bend it out of the way, if desired, during insertion of the introducer 20 or other instrument. In one embodiment, the body may be fabricated from a relatively flexible material, including a plastic material such as a polycarbonate (e.g., MAKROLON). However, it is to be understood that the stick may be fabricated from any suitable material apparent to one of skill in the art.

The introducer is configured to deliver virtually any prosthetic repair fabric 28 which is collapsible into a slender configuration. The introducer is particularly suitable for delivering sheets of prosthetic repair fabric into the abdominal cavity for use in the repair of inguinal or ventral hernias. An exemplary fabric is knitted polypropylene monofilament mesh fabric available from C.R. Bard, Inc., under the brand name BARD MESH. When implanted, the polypropylene mesh stimulates an inflammatory reaction which promotes rapid tissue ingrowth into and around the mesh structure. Another exemplary fabric is a combination of a mesh fabric layer and an adhesion resistant barrier layer available from C.R. Bard, Inc., under the brand name BARD COMPOSIX E/X. The barrier layer inhibits adhesions to one side of the mesh layer.

Other prosthetic materials which are suitable for tissue reinforcement and/or defect closure include PROLENE and MERSILENE. Also, DACRON or TEFLON textile based meshes, microporous polypropylene sheeting (CELGARD), and expanded PTFE (GORETEX) may be used. Absorbable meshes, including polyglactin (VICRYL) and polyglycolic acid (DEXON), may also be loaded and delivered using the present invention.

Non-tissue infiltratable fabrics also may be employed in the delivery and loading device. Silicone elastomer sheeting, such as SILASTIC Rx Medical Grade Sheeting (Platinum Cured) distributed by Dow Corning Corporation, would be suitable. The silicone elastomer sheeting may be reinforced with DACRON or other reinforcing materials. It is contemplated that oxidized, regenerated cellulose (Intercede (TC7)) also may be employed with the present invention. Other materials also may be utilized as will be apparent to those of skill in the art.

Having described several embodiments of the invention in detail, various modifications and improvements will readily occur to those skilled in the art. Such modifications and improvements are intended to be within the spirit and scope of the invention. Accordingly, the foregoing description is by way of example only and is not intended as limiting. The invention is limited only as defined by the following claims and the equivalents thereto.

The invention claimed is:

1. A method of delivering a prosthetic fabric into a patient, the method comprising acts of:
   (a) collapsing the prosthetic fabric from a first configuration to a collapsed configuration using a first portion of a dual-purpose component;
   (b) loading the prosthetic fabric in the collapsed configuration into a delivery tube through a proximal end thereof using the first portion of the dual-purpose component in a first orientation;
   (c) following act (b), removing the dual-purpose component from the proximal end of the delivery tube, reversing the dual-purpose component from the first orientation to a second orientation and inserting the dual-purpose component into the delivery tube in the second orientation through the proximal end thereof; and
   (d) expelling the prosthetic fabric in the collapsed configuration from a distal end of the delivery tube using a second portion of the dual-purpose component in the second orientation.

2. The method according to claim 1, wherein act (a) includes rolling the prosthetic fabric about the first portion of the dual-purpose component in the first orientation.

3. The method according to claim 1, wherein act (b) includes loading the prosthetic fabric through an aperture at the proximal end of the delivery tube.

4. The method according to claim 1, wherein act (d) includes limiting travel of the dual-purpose component through the delivery tube in the second configuration.

5. The method according to claim 1, wherein act (c) includes maintaining the prosthetic fabric in the delivery tube.

6. The method according to claim 1, further comprising an act of:
   (e) prior to act (d), inserting the delivery tube into the patient to a predetermined depth.

7. The method of claim 6, wherein act (e) includes adjusting the predetermined depth.

* * * * *